Figure 1:
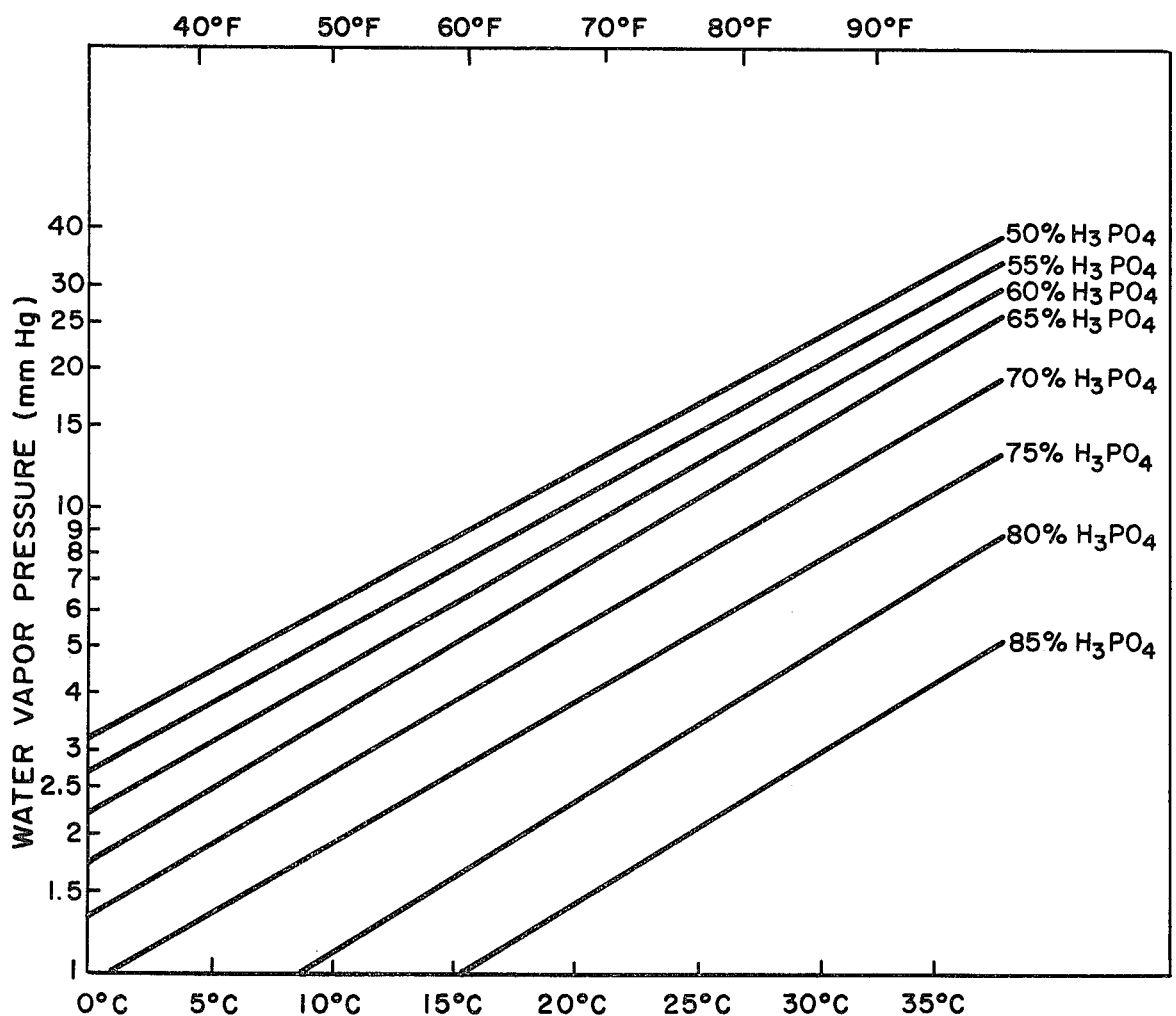
Figure 2:
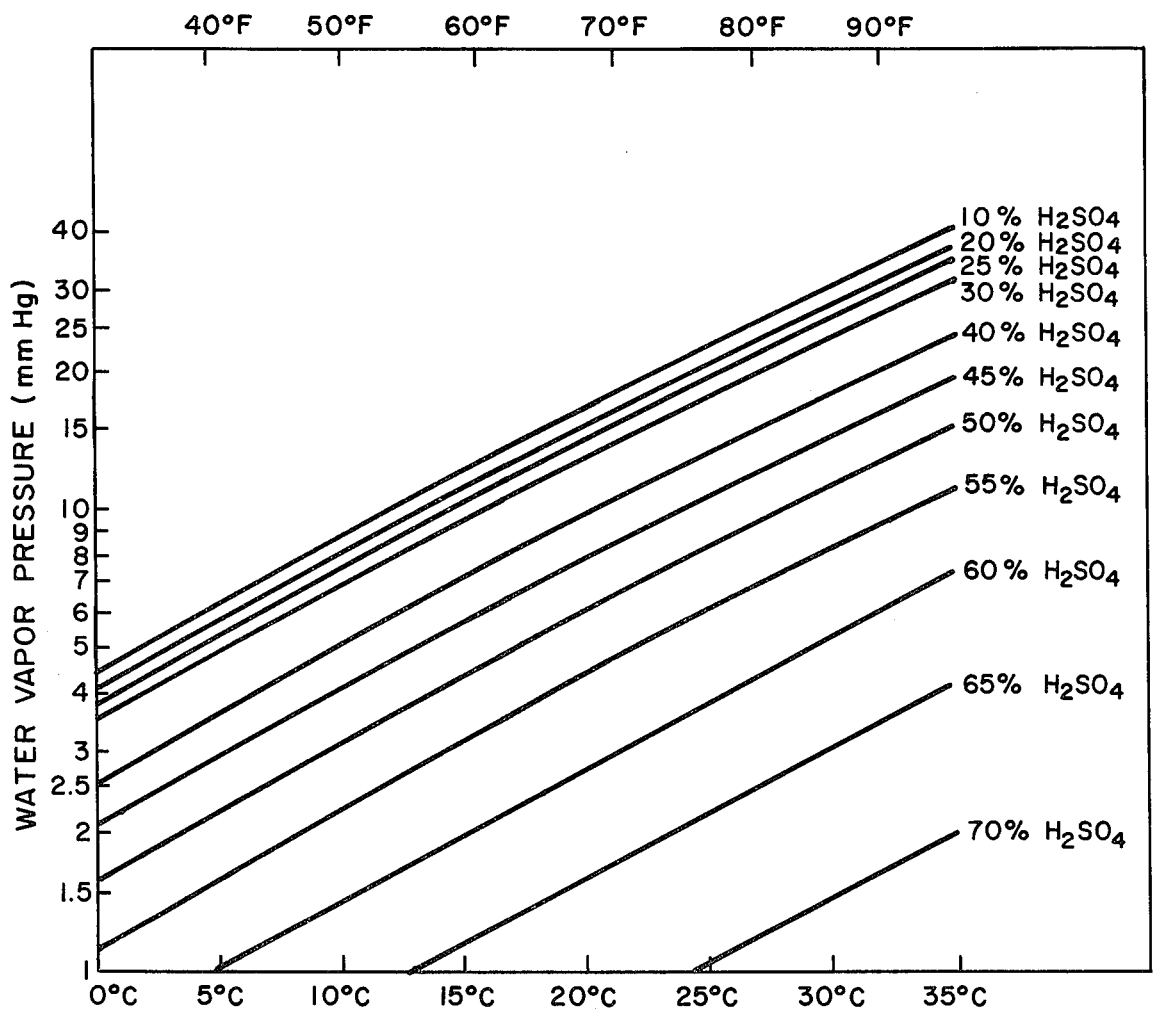

United States Patent [19]

O'Neill et al.

[11] 4,107,268

[45] Aug. 15, 1978

[54] ANIMAL CONFINEMENT ENVIRONMENT CONTROL

[75] Inventors: Eugene T. O'Neill, Hightstown, N.J.; Donald O. Flach, Mamaroneck, N.Y.

[73] Assignee: FMC Corporation, Philadelphia, Pa.

[21] Appl. No.: 703,915

[22] Filed: Jul. 9, 1976

[51] Int. Cl.$^2$ ............................................. B01D 53/34
[52] U.S. Cl. .................................... 423/210; 423/224; 423/245; 21/55; 21/58; 55/29; 119/15; 119/16; 119/17; 119/19; 119/20
[58] Field of Search .............. 423/210, 224, 245; 21/55, 58; 119/16, 22, 28, 15, 19, 20; 55/29

[56] References Cited

U.S. PATENT DOCUMENTS

| Re. 26,183 | 4/1967 | Morrell | 119/16 |
| 1,431,981 | 10/1922 | Richter | 55/29 |
| 1,644,439 | 10/1927 | Muller | 55/29 |
| 3,905,774 | 9/1975 | Kotting | 423/210 |
| 3,924,571 | 12/1975 | Holman | 119/15 |
| 3,969,479 | 7/1976 | Lonnes et al. | 423/224 |

FOREIGN PATENT DOCUMENTS 1,152,705  5/1969  United Kingdom ............ 423/224

Primary Examiner—Earl C. Thomas

[57] ABSTRACT

Process for controlling the humidity of a closed animal confinement habitat and air by contacting the habitat air with an aqueous solution containing sufficient amounts of hydrogen peroxide and a mineral acid to absorb and oxidize the odorous and noxious gases from the air and to maintain the humidity level of the contacted air as desired between 40% and 95% relative humidity.

6 Claims, 2 Drawing Figures

ANIMAL CONFINEMENT ENVIRONMENT CONTROL

This invention relates to a process for controlling the humidity of a closed animal confinement habitat while preventing undesirable buildup of odorous and noxious gases therein.

In recent years, the raising of animals in confined areas, such as animal confinement habitats, has become commonplace. This trend is a result of several factors, including increased technology in the livestock industry, and increased population and weight gain of confined animals over pasture and yard animals. A drawback of the confinement habitat, however, is the formation of noxious and odorous gases resulting from anaerobic microbial decomposition of animal wastes dropped into and temporarily stored in storage or collection pits located beneath the habitat floor.

The predominant gases generated within animal confinement habitats are carbon monoxide, ammonia, hydrogen sulfide, methane and trace quantities of numerous organic compounds such as mercaptans and skatole. These gases must be removed from the habitat air to assure effective animal physiology; primarily production and growth, as well as removed in a manner that will not adversely effect other habitat environmental factors, such as temperature and humidity, which likewise influence animal physiology.

Various ventilation systems have been proposed for removing animal confinement habitat air and processes for treating the same, which systems may include means for heating, cooling, dehumidifing, humidifing, and air cleaning. These ventilation systems, however, have been economically unable to attain a steady state condition wherein the desired air purification and air exchange rate is achieved while maintaining constant humidity conditions in the habitat. Generally, ventilation systems simply rely upon fans and blowers to achieve air exhaust, which systems induce drafts by pulling in cold or heat, humidity, dust and other pollutants which are not only detrimental to animal physiological well being, but which place severe strains on the system itself, such as in the heating, humidifying and/or air conditioning means. In addition, when the outside air temperature is substantially cooler than the inside air temperature not enough air can be ventilated to significantly reduce odorous and noxious gas levels without reducing inside air temperature to undesirable low levels. Furthermore, most ventilation systems do not efficiently remove the heavier than air hydrogen sulfide which remains near the habitat floor. Ventilation systems employed under the floor slats, while being able to remove hydrogen sulfide, are ineffective during the cooler times of the year since these systems undesirably cool the floor and likewise endanger animal physiology.

A process has been unexpectedly discovered, for controlling the humidity of a closed animal confinement habitat and purifying the habitat air to prevent undesirable buildup of odorous and noxious gases, which comprises; removing a portion of the air from the confinement habitat, said air containing odorous and noxious gases; contacting the removed air with an aqueous solution containing 0.01% to 1.0% by weight hydrogen peroxide and 10% to 85% by weight of a mineral acid selected from the group consisting of phosphoric acid and sulfuric acid, said air and aqueous solution having essentially the same temperature; absorbing and oxidizing the odorous and noxious gases in said aqueous solution; adjusting the mineral acid concentration during the contacting step to maintain the humidity level of the contacted air to the desired level between 40% and 95% relative humidity; and passing the air back into the confinement habitat.

The process of this invention permits the removal of essentially all of the odorous and noxious gases from the habitat air in an effective and efficient manner while controlling habitat air humidity. The process of the invention also reduces fuel costs, eliminates floor-level drafts and floor to ceiling temperature gradients without the necessity for employing costly dehumidification or humidification means. In addition, this process curtails the transmission of air-borne, disease-causing pathogens by the sterlizing action of the contacting solution, thus resulting in fewer animal mortalities, faster weight gain, or increased milk or egg production.

FIG. I represents a phosphoric acid concentration graph which is used to determine the acid concentration corresponding to the desired relative humidity from 40° to 90° F.

FIG. II represents a sulfuric acid concentration graph which is used to determine the acid concentration corresponding to the desired relative humidity from 40° to 90° F.

In the process of this invention, a portion of the air containing odorous and noxious gases is removed from the confinement habitat and contacted with an aqueous solution containing hydrogen peroxide and a mineral acid. The aqueous solution preferably contains 0.01% to 1.0% by weight hydrogen peroxide and most preferably 0.1% to 1.0% by weight hydrogen peroxide which amounts are sufficient to oxidize substantially all of the oxidizable gases present in the habitat air.

Hydrogen peroxide can be used either in the free state or combined as the peroxyhydrates of inorganic salts which break down in an aqueous media to yield hydrogen peroxide. Examples of such salts are sodium metaborate peroxyhydrate and sodium carbonate peroxide. It is preferred to use the free state of hydrogen peroxide since its oxidation by-product is water and if it breaks down it converts to water and oxygen and does not leave any foreign residue in the aqueous solution.

The hydrogen peroxide in the aqueous solution may be optionally stabilized by conventional methods to limit hydrogen peroxide decomposition, such as by employing magnesium oxide or other stabilizers in the aqueous solution. Likewise, conventional metal catalysts may also be employed to assist in the oxidation reaction. These catalysts include salts of iron, cobalt, nickel, copper, manganese, molybdenum, vanadium, platinum, palladium and silver. If a catalyst is employed, the first four catalytic salts are preferred. The catalyst can be employed with or without conventional complexing agents such as gluconic and citric acid.

The mineral acids employed in the invention are phosphoric acid and sulfuric acid, which may be employed singly or in combination. These mineral acids are employed since they have a favorably low vapor pressure, they add practically no toxic, irritating or corrosive fumes to the air being contacted, they do not actively cause the decomposition of hydrogen peroxide, and they are effective in neutralizing ammonia and organic amine gases. In general, the aqueous solution will contain 10% to 85% by weight of the mineral acid and preferably contains 30% to 70% by weight phosphoric acid or 25% to 50% by weight sulfuric acid.

The confinement habitat air is contacted with the aqueous solution in any conventional gas-liquid contacting device, providing the device has a means for preventing any mists of aqueous solution from being recycled with the purified air. The contacting device may be a vertical packed bed or tower, a horizontal, single or multi-chambered cross-flow unit, a spray chamber or any other device that will accomplish adequate contacting. The habitat air and aqueous solution may be fed into the contactor either counter-currently, cross-currently or co-currently provided enough gas-liquid interface area is provided for a sufficient period of time to effect absorption and/or oxidation of the unwanted contaminant. Preferably, the confinement habitat air is removed from the confinement habitat at a rate between 1% and 5% of the total volume of confinement habitat air per minute. These rates are generally sufficient to maintain the odorous and noxious gas content in the confinement habitat at acceptably low levels.

The time necessary to contact the confinement habitat air must be sufficient for the aqueous solution to absorb and oxidize the odorous and noxious gases. Contact times of less than one second up to fifteen seconds have been found sufficient to completely absorb and oxidize the inorganic odorous and noxious gaseous contaminants from the air. Longer contact times may be necessary to absorb and oxidize some gaseous organic sulfur compounds. These latter times range from one to sixty seconds depending upon the specific gaseous organic sulfur compounds being removed.

The contactor may be operated in a continuous or batch-wise manner. When operated continuously, the hydrogen peroxide and mineral acid are added to the contactor either separately or as a mixture in the amounts needed. During operation, additional hydrogen peroxide and/or mineral acid is added to replace that amount consumed by the chemical reaction, again either separately or as a mixture. When the contactor is operated in a batch-wise manner, the requisite amounts of hydrogen peroxide and mineral acid are added and periodically the spent solution is removed, discarded and replaced with fresh aqueous solution.

Any pattern of air circulation within the confinement house may be used in the practice of this invention. An especially effective procedure involves removing the particularly objectionable hydrogen sulfide through ducts positioned within the space between the slotted floor and the waste storage pit liquid level. In this way, all of the odorous and noxious gases are passed into the contactor for treatment promptly after formation and the confinement habitat environment is maintained as fresh as practicable. After the air has been purified, the cleaned air, after being optionally heated or cooled to the desired habitat temperature, is passed back into the confinement habitat by overhead distributors extending the length of the structure. The air is then preferably forced to casually flow downward over the animals and once again be drawn into the ducts below the slotted floor. This procedure permits efficient and thorough purification and circulation of the habitat air with few drafts and minimum overhead to floor temperature variations. It should be recognized however, that other effective systems for achieving air circulation may be employed in the practice of this invention.

Humidity control is achieved by adjusting the mineral acid concentration during the contacting step within specifically defined limits so that the water vapor pressure of the air and the aqueous solution approach identical values as the air contacts the aqueous solution. At any given habitat and aqueous solution temperature, air which enters the aqueous solution with a water vapor pressure either less than or greater than the water vapor pressure of the aqueous solution, which vapor pressure is dependent upon mineral acid concentration, will absorb or lose sufficient water to the aqueous solution, respectively, so that the final water vapor pressure of both aqueous solution and air are equal. For example, confinement habitat air having a temperature of 77° F and a 50% relative humidity entering a contactor having an aqueous solution operated at the same temperature with 62% by weight phosphoric acid will neither add nor remove moisture from the air. The same result would be expected with an aqueous solution containing 43% by weight sulfuric acid.

Until a steady state condition is achieved, it will be necessary to make minor adjustments in temperature and/or mineral acid concentration during contacting to establish a constant relative humidity in the air passed into the confinement habitat and the air entering the contactor. For example, if the air entering the contactor containing the aqueous solution having the 62% by weight phosphoric acid changed from 50% to 38% relative humidity, such as would occur by varying the number of animals in the confinement habitat or the quantity or humidity of the fresh air introduced into the habitat, the air would pick up water and the aqueous solution volume would decrease, acid concentration increase and new equilibrium conditions develop. In a similar manner, when the relative humidity of the air would increase from 50% to 62%, the air would loose water and the aqueous solution volume would increase, acid concentration decrease, and new equilibrium conditions develop.

Maintenance of the habitat air and aqueous solution at essentially the same temperature is necessary to effectively control relative humidity. While the exact temperatures that can be employed vary from 40° F to 90° F, it is preferred to employ temperatures from 65° F to 85° F for effective animal physiological well being and for the rapid absorption and oxidation of the odorous and noxious gases from the confinement habitat air.

The necesaary aqueous solution mineral acid concentration to achieve particular relative humidity conditions is determined by initially establishing the vapor pressure of water at a given temerature from Table I for the desired relative humidity. Table I represents the vapor pressure of water at relative humidities between 40% and 95% from 40° to 90° F. The acid concentration which must be present in the aqueous solution to achieve this relative humidity is determined from FIG. I for phosphoric acid or FIG. II for sulfuric acid by finding the vapor pressure of water on the vertical scale and desired temperature on the horizontal scale. The acid concentration is defined as the point where these scales intercept.

By employing the above procedure for determining mineral acid concentrations, the following broad ranges are established. Air passing through an aqueous solution containing 10% to 85% by weight phosphoric acid will have a relative humidity between 40% and 95%, when the air and aqueous solution temperatures are between 40° F and 90° F. When the aqueous solution contains 30% to 70% by weight phosphoric acid or 25% to 50% by weight sulfuric acid within the same temperature range, the air passing through the solution will have a relative humidity between 50% and 80%. These relative humidities and temperatures are ideal for animal confinement habitat populations.

Any commercially available hygrometer is used to measure the relative humidity of the purified air leaving the contactor. When it is desired to change the relative humidity in the habitat and the relative humidity in the purified air, the required amount of mineral acid or water is added to the aqueous solution either manually or automatically to either increase or decrease the water vapor pressure of the aqueous solution. Alternatively, a portion of the aqueous solution is removed from the contactor and the mineral acid concentration measured by conventional analytical titration means, whereupon mineral acid or water is added to the aqueous solution to adjust the water vapor pressure of the aqueous solution to the appropriate level.

The following examples are given to illustrate the invention but are not deemed limiting thereof. All percentages given are based upon weight unless otherwise indicated.

EXAMPLE

A closed animal confinement habitat containing 40 pens for farrowing sows was equipped with a stainless steel vertical packed tower contactor measuring 92 inches high by 24 inches diameter which contained 3 inch polyethylene Intalox ® saddles. The bottom section of the contactor had a 23 gallon reservoir for receiving and retaining aqueous solution. A recirculating pump transferred the aqueous solution from the reservoir to the top of the tower where the solution was permitted to pass downward through the contactor. Air intake pipes, connected to the lower portion of the contactor for counter-current flow, were hung from the ceiling on opposite sides of the habitat. Each air intake pipe was connected to 16 by 8 inch galvanized duct piping which extended parallel to the floor for approximately 100 feet. Ten 6 inch diameter drop pipes evenly spaced along the duct piping extended to the slotted floor just above the waste collection pits. The end of each drop pipe was flared to 24 inches by 9 inches to effectively draw air from the waste collection pits below the floor.

Air was removed from the confinement habitat through the drop pipes at a rate of 1000 cubic feet per minute, passed through the contacting apparatus wherein it was purified with an aqueous solution containing 0.8% by weight hydrogen peroxide, 65% by weight phosphoric acid, and the remainder tap water. The aqueous solution was maintained at 80° F. The purified air was then returned to the confinement habitat after passing through a heater which maintained the purified air temperature at 80° F. The air was distributed in the confinement habitat through overhead duct work extending the entire length of the habitat.

The relative humidity of the purified air and aqueous solution mineral acid concentration were routinely tested, the former with a conventional hygrometer, the latter by a conventional laboratory analytical titration method employing a sodium hydroxide solution and an acid-base indicator. Additional quantities of hydrogen peroxide and phosphoric acid were added intermittantly to maintain aqueous solution integrity. By maintaining solution integrity as well as air and solution temperatures at 80° F the relative humidity of the purified air passing into the habitat was maintained at 50%, and removal of hydrogen sulfide and ammonia was essentially 100% effective. Hydrogen sulfide and ammonia were used as indicators of odorous and noxious gases because of the relative simplicity by which the presence of these gases can be measured. The results are set forth in Table II.

To determine the effectiveness of the exemplified process upon animal physiological well being, an equivalent closed animal confinement habitat was used during the same time period which contained essentially the same number of animals and same initial environmental conditions without the exemplified contacting tower and recirculation means. The uncontrolled habitat, however, was equipped with a ventilation fan that exhausted the habitat air at a rate of 1000 cubic feet per minute. The results are set forth in Table II.

The results indicate that at weaning, the average weight of pigs raised in the habitat controlled by the process of the invention was 2.92 lbs. or 23% greater than the pigs raised in the uncontrolled habitat.

The invention being thus described, it will be obvious that the same may be varied in many ways. Such variations are not to be regarded as a departure from the spirit and scope of the invention, and all such modifications are intended to be included within the scope of the following claims.

TABLE 1

| TEMPERATURE | | WATER VAPOR PRESSURE (mm Hg) % RELATIVE HUMIDITY | | | | | | |
|---|---|---|---|---|---|---|---|---|
| °F | °C | 40 | 50 | 60 | 70 | 80 | 90 | 95 |
| 40 | 4.4 | 1.32 | 1.65 | 1.98 | 2.31 | 2.64 | 2.97 | 3.14 |
| 50 | 10.0 | 3.68 | 4.60 | 5.52 | 6.44 | 7.36 | 8.28 | 8.74 |
| 60 | 15.6 | 5.28 | 6.60 | 7.92 | 9.24 | 10.56 | 11.88 | 12.54 |
| 70 | 21.1 | 7.52 | 9.40 | 11.28 | 13.16 | 15.04 | 16.92 | 17.86 |
| 80 | 26.7 | 10.48 | 13.10 | 15.72 | 18.34 | 20.96 | 23.58 | 24.89 |
| 90 | 32.2 | 14.44 | 18.05 | 21.66 | 25.27 | 28.88 | 32.49 | 34.30 |

Table II

| Data | Controlled Habitat | Uncontrolled Habitat |
|---|---|---|
| Number of pigs born live | 323 | 251 |
| Average litter size at birth | 8.29 | 7.97 |
| Average weight of pigs at birth | 3.01 lbs. | 2.96 lbs. |
| Average difference in weight | 0.05 lbs. | |
| Number of pigs at 2 weeks weight | 283 | 196 |
| Average weight of pigs after 2 weeks | 8.43 lbs. | 7.40 lbs. |
| Average difference in weight | 1.03 lbs. | |
| Average litter size after 2 weeks | 7.45 | 6.32 |
| Average difference between birth weight & 2 week weight | 5.42 lbs. | 4.44 lbs. |
| Average difference in weight | .98 lbs. | |
| Average litter size at weaning | 7.26 | 6.16 |
| Average weight of pigs at weaning | 15.52 lbs. | 12.55 lbs. |
| Average difference in weight | 2.97 lbs. | |
| Average difference between 2 week weight and weaning weight | 7.09 lbs. | 5.15 lbs. |
| Average difference between birth weight and weaning weight | 12.51 lbs. | 9.59 lbs. |
| Average difference in weight | 2.92 lbs. | |
| Average weight gain per day from birth to 2 week weight | 0.40 lbs. | 0.33 lbs. |
| Average weight gain per day from 2 weeks weaning weight | 0.43 lbs. | 0.36 lbs. |

Table II-continued

| Data | Controlled Habitat | Uncontrolled Habitat |
| --- | --- | --- |
| Average weight gain per day from birth to weaning | 0.42 lbs. | 0.34 lbs. |

What is claimed is:

1. A process for controlling the humidity of a closed animal confinement habitat and purifying the habitat air to prevent undesirable buildup of odorous and noxious gases, which comprises:

removing a portion of the air from the confinement habitat, said air containing odorous and noxious gases;

contacting the removed air with an aqueous solution containing 0.01% to 1.0% by weight hydrogen peroxide and 10% to 85% by weight of a mineral acid selected from the group consisting of phosphoric acid and sulfuric acid, said air and aqueous solution having essentially the same temperature;

absorbing and oxidizing the odorous and noxious gases in said aqueous solution;

adjusting the mineral acid concentration during the contacting step to maintain the humidity level of the contacted air to the desired level between 40% and 95% relative humidity; and passing the air back into the confinement habitat.

2. The process of claim 1, wherein the aqueous solution contains 0.1% to 1.0% by weight hydrogen peroxide.

3. The process of claim 1, wherein the aqueous solution contains 30% to 70% by weight phosphoric acid.

4. The process of claim 3, wherein the air passing into the confinement habitat has a relative humidity between 50% and 80%.

5. The process of claim 1, wherein the aqueous solution contains 25% to 50% by weight sulfuric acid.

6. The process of claim 5, wherein the air passing into the confinement habitat has a relative humidity between 50% and 80%.

* * * * *